United States Patent [19]

Haber et al.

[11] Patent Number: 4,478,827
[45] Date of Patent: Oct. 23, 1984

[54] RENIN INHIBITORS

[75] Inventors: Edgar Haber, Weston; James Burton, Amesbury, both of Mass.

[73] Assignee: The General Hospital Corporation, Boston, Mass.

[21] Appl. No.: 492,835

[22] Filed: May 9, 1983

[51] Int. Cl.³ .................... C07C 103/52; A61K 37/02
[52] U.S. Cl. .............................. 424/177; 260/112.5 R
[58] Field of Search ...................... 424/177; 260/112.5

[56] References Cited

U.S. PATENT DOCUMENTS 4,269,827  5/1981  Burton et al. ................ 260/112.5 R

OTHER PUBLICATIONS

Chemical Abstracts, 86, 147 (1977), Abst. No. 27224p.
Chemical Abstracts, 97, 18117 (1982), Abst. No. 18120b.

Primary Examiner—Delbert R. Phillips
Assistant Examiner—F. T. Moezie
Attorney, Agent, or Firm—Saidman, Sterne & Kessler

[57] ABSTRACT

A compound of the formula

Z-His-Pro-Phe-His-X-X-Val-Tyr-(D-)-Y wherein the Xs are the same or different and selected from the group consisting of an aromatic, a chlorinated aromatic, an aliphatic and a chlorinated aliphatic amino acid residue;

Y is a positively or negatively charged amino acid residue; and

Z is a proline or a polyprolyl residue having up to 5 prolyl residues, is useful for decreasing renin-related high blood pressure.

6 Claims, No Drawings

RENIN INHIBITORS

BACKGROUND OF THE INVENTION

The Government has rights in this invention under Grant No. 2 R01 19517 by the National Institutes of Health.

tensin II by removing the amino terminal aspartic acid. The resultant heptapeptide, sometimes called angiotensin III, is believed by some investigators to be the primary mediator of adrenal cortical aldosterone secretion. Angiotensin II and III have very short half-lives in the circulation and are further degraded to smaller inactive peptides.

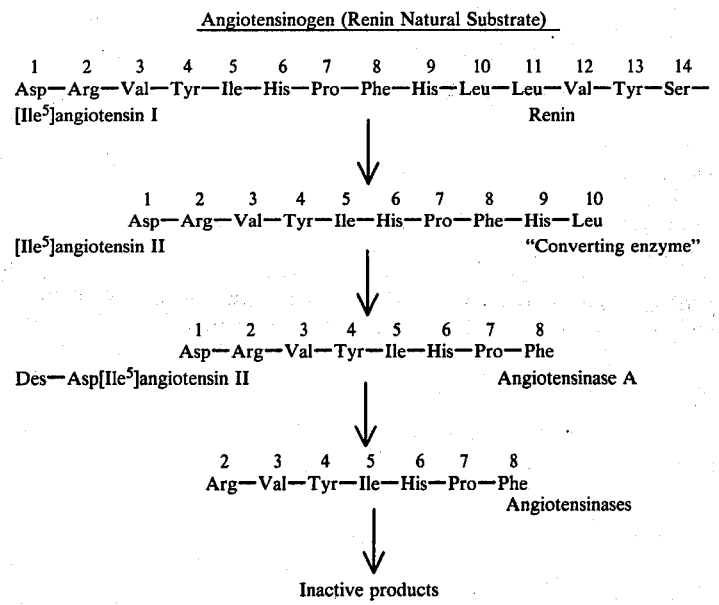

FIELD OF THE INVENTION

This invention relates to a method and composition using renin inhibitors for reducing blood pressure.

BRIEF DESCRIPTION OF THE PRIOR ART

Renin (E.C. 3.4.99.19) is a proteolytic enzyme released into the blood in response to a variety of stimuli. Once in the plasma, renin cleaves a specific peptide bond in its natural protein substrate, angiotensinogen, to yield angiotensin I. Renin has no known direct physiologic effect other than to cleave its substrate. Angiotensin I has no known biological activity, although several workers have shown that it binds and blocks the angiotensin II receptor. Angiotensin I is rapidly cleaved by the carboxydipeptidase-converting enzyme (E.C. 3.4.15.1), to yield angiotensin II. Angiotensin II has many biological activities including increasing blood pressure both directly by a vasoconstrictor response and indirectly by sodium and fluid retention. Excessive release of renin, in a variety of pathological conditions, can thus result in lifethreatening hypertension. Accordingly, there has been a concerted research effort aimed at providing means which inhibit renin and prevent generation of angiotensin I and II, thereby to provide a means for reducing hypertension.

The amino acid sequence of the amino terminal 14 residues of equine renin substrate is shown schematically below. Preliminary evidence indicates substantial differences may exist in the amino acid sequence of natural substrate from other species. Renin cleaves this protein substrate between the leucyl residues at position 10 and 11 to release the decapeptide angiotensin I. Angiotensin I is in turn cleaved between residues 8 and 9 by converting enzyme to yield the active hormone, angiotensin II. Aminopeptidases further degrade angio- Two types of agents that block steps in the generation of angiotensin in man have been used prior to this invention. They are: converting enzyme inhibitors and angiotensin receptor blockers.

Angiotensin converting enzyme blockers such as teprotide and captopril, which block the conversion of the decapeptide angiotensin I to the active angiotensin II also prevent the degradation of the vasodilating hormone bradykinin. Excessive concentrations of bradykinin are believed to cause undesirable effects, including hypotension.

Angiotensin receptor blockers are analogs of angiotensin II and have all been shown at certain dose ranges in all individuals to be partial agonists and to increase blood pressure.

Two classes of renin inhibitors have been developed and undergone some testing. One class of compounds are analogs of lysolecithin. These materials have low affinity for renin and are unlikely to be useful drugs. The second class of compounds, pepstatins, are bacterial products. They inhibit all acid proteases including enzymes such as pepsin and cathepsin D and are thus relatively non-specific. Pepstatin and semi-synthetic derivatives of these compounds have been tested in experimental animals. Their relatively lower binding affinity for renin than for other enzymes as well as their lack of selectivity make it unlikely that they will be utilized in clinical applications.

The person skilled in this art thus is reluctant to utilize these agents in hypertension control. Therefore, it would be desirable to provide a means for inhibiting the action of renin on its natural substrate by competing with the natural substrate for the active binding site of the renin molecule.

As disclosed in the prior art, it has been found that the octapeptide, His-Pro-Phe-His-Leu-Leu-Val-Tyr, is the smallest peptide component of the tetradecapeptide substrate which functions effectively as a substrate for renin. Accordingly, it has been proposed in the prior art to provide modifications of this molecule and other similar fragments from the natural substrate which would function as a competing inhibitor for the reaction between renin and its substrate.

A wide variety of such substitute compounds have been proposed, wherein different amino acids replace component amino acids in the active octapeptide. A large number of such synthetic peptides have been found to be active as inhibitors for renin in vitro. For example, modification of the octapeptide inhibitor by replacing either leucyl residue with the D-enantiomorph yields inhibitors which are not cleaved by renin. In addition, the [D-leu$^6$]octapeptide binds renin one order of magnitude more tightly than the parent octapeptide at pH 5.5. Attempts to inhibit renin with this modified octapeptide at pH 7.5 indicate it to be inactive at this pH. Therefore, this modified octapeptide is useless for in vivo application. In addition, it has been proposed to add one or more proline molecules to the N-terminal histidine of the octapeptide, thereby to improve solubility at physiologic pH. However, while some solubility improvement has been noted, inhibition activity is still too low for the resultant modified peptide to be useful for in vivo application. Replacement of the valyl residue with threonyl at the seven position of the octapeptide provides an octapeptide which is twice as soluble at physiologic pH but is a very poor inhibitor of renin. Attempts to increase solubility by modifying the C-terminus carboxyl of the peptide such as by the addition of serinol has not resulted in the expected solubility of the resultant product. Furthermore, various attempts to improve solubility by the addition of charged groups to the N-terminus of various renin inhibitors have not resulted in increased solubility which would permit in vivo application of the resultant product for use as a renin inhibitor. Attempts also have been made to increase binding while retaining the desired solubility of peptides by substituting amino acids at the binding site of the active octapeptide. Thus, for the series of octapeptides containing Leu-Tyr, Leu-Phe, Phe-Phe rather than the Leu-Leu at the cleavage site of natural substrate, binding constants of 12, 4, and 1$\mu$ M, respectively have been obtained. However, none of these compounds has the requisite half-life to afford sufficient utility for in vivo use.

In U.S. Pat. No. 4,269,827 by the present co-inventors is described a family of compounds of the formulae (1)

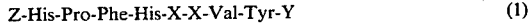
(1)

wherein the Xs are the same or different and are aromatic or aliphatic amino acid residues, Y is a charged amino acid, and Z is proline, hydroxyproline, thioproline or polyproline having up to 5 prolyl residues. These compounds are suggested as compositions which inhibit renin in vivo and reduce blood pressure. Foremost among these compounds is Pro-His-Pro-Pre-His-Phe-Phe-Val-Tyr-Lys (hereinafter "RIP").

RIP and its analogues of formulae (1) represented a substantial advance in the art since they were the first peptides which bind to renin, having substantial solubility in blood. However, RIP has been found to have relatively short life both in vitro and in vivo, and to be substrate for angiotensin converting enzyme in vitro. Also, RIP crossreacts with some of the antisera used in the radioimmunoassay (RIA) for renin activity.

Accordingly, it is still highly desirable to provide a renin inhibitor which has high binding activity for renin at physiological pH, which would show long half-life in vivo, and which would be useful for the treatment of renin-related high blood pressure.

SUMMARY OF THE INVENTION

The present invention provides peptide compositions which are active in binding renin at physiologic pH and which are soluble in human plasma. In addition, the present invention provides peptide compositions which have a sufficiently long half-life to afford their use in vivo for the purpose of binding significant amounts of renin present in the blood of a patient.

The peptide of this invention are prepared by solid phase peptide synthesis wherein protected amino acids are anchored to a polymeric substrate and are sequentially added one on to another until the desired amino acid sequence is attained. Thereafter, the peptide is cleaved from the polymer substrate with concomitant removal of the side chain protecting groups. The resultant polypeptide then is purified by chromatography.

The peptides of this invention have been found to be significantly effective in reducing blood pressure in vivo in primates.

The compounds of the invention are those having the formulae (2)

(2)

wherein the Xs are the same or different and are aromatic, or chlorinated aromatic or aliphatic or chlorinated aliphatic amino acid residues, Y is a charged amino acid residue selected from the group consisting of lysine, arginine, aspartic and glutamic acid and their $\alpha$-carbon esters of lower aliphatic alcohols, and their primary or secondary lower aliphatic amides, and Z is selected from the group consisting of proline, thioproline, hydroxyproline and polyproline having up to 5 prolyl residues.

DESCRIPTION OF THE PREFERRED EMBODIMENTS

The peptides of the present invention are represented by formula (2):

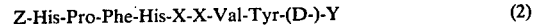
(2)

wherein His is histidine, Pro is proline, Phe is phenylalanine, Val is valine and Tyr is tyrosine. The Xs are the same or different and are an aromatic or aliphatic amino acid. These may be selected from the group consisting of phenylalanine, a chlorinated phenylalanine such as chlorophenylalanine, dichlorophenylalanine, tyrosine, leucine, glycine, isoleucine, valine or the like. Y is a charged amino acid residue at the C-terminus of the polypeptide which can be either positively or negatively charged including lysine, arginine, ornithine, aspartic or glutamic acid and their $\alpha$-carbon esters of lower aliphatic alcohols ($C_1$-$C_6$) and their primary or secondary lower ($C_1$-$C_6$) aliphatic amides. This charged amino acid residue has the effect of both extending the half-life of the polypeptide molecule in vivo and increasing its solubility, thereby to render the polypeptide effective in inhibiting renin in vivo. Z can be either proline, hydroxyproline, thioproline or polyproline having up to about 5 prolyl residues in series. The proline or polyproline residue both renders the polypeptide molecules specific for primate renin, and increases solubility.

Particularly useful polypeptides for purposes of the present invention are those wherein Z is proline, Y is lysine and the Xs can be the same or different and can be phenylalanine or monochlorophenylalanine.

The polypeptides of this invention are characterized by solubility in an aqueous medium at physiological pH of 100–500 μm, an inhibition constant for ($K_i$) of between 1–50 μm and a half-life in vivo, as measured by rate of loss of radioactively labeled peptide from the circulation, of between about 1–10 minutes, especially 5–10 minutes.

The most important structurally distinguishing feature of the compounds of the present invention relative to those of U.S. Pat. No. 4,269,827 as represented by formula (1), supra, is that the Y residue in the present invention is of the D-configuration. This allows the peptides of the present invention to resist degradation by carboxypeptidases, carboxydipeptidases, and other proteolytic enzymes that attack the C-terminus of peptides.

Particularly suitable peptide products obtained by this invention are:
Pro-His-Pro-Phe-His-Phe-Phe-Val-Tyr-D-Lys (3)
Pro-His-Pro-Phe-His-Leu-Phe(Cl)-Val-Tyr-D-Lys (4)
Pro-His-Pro-Phe-His-Leu-Tyr-Val-Tyr-D-Lys (5)
Pro-His-Pro-Phe-His-Leu-Phe-Val-Tyr-D-Lys (6)
Compound (3) will hereinafter be referred to as "D-RIP".

The polypeptides of this invention can be produced by any conventional means for joining amino acid residues to form a polypeptide chain. A particularly desirable procedure involves solid phase peptide synthesis wherein amino acid residues are joined sequentially to a polymer base, under reaction conditions to protect the amino acids until the desired peptide sequence is formed. Thereafter, the peptide chain is cleaved from the polymer base and the constituent amino acid side chains are deprotected. This yields the desired peptide sequence which then can be purified, such as by chromatography.

A suitable polymer base comprises beads formed from polystyrene wherein a portion of the phenyl groups are substituted with $CH_2Cl$ portions. The first amino acid bonded to the polymer is the amino acid which ultimately becomes the charged residue at the C-terminus of the final peptide chain. Bonding is conveniently effected by reacting the protected amino acid with the chloromethylated polymer under condensation conditions to establish an ester linkage between the C-terminal amino acid and the polymer. Suitable conditions to effect the desired condensation while maintaining protection of the amino group and side chain of the acid are to reflux with triethylene in alcohol for 24 hours. When the amino acid residue has more than one imino or amino group, the imino or amino group which is to be linked by an amide bond with the next succeeding amino acid residue is protected less strongly than the other amino or imino groups, which are to remain protected throughout formation of the desired peptide. After the first amino acid has been bonded to the polymer substrate, the next amino acid is added by the following procedure. Generally, the protected amino acid on the polymer is first deprotected at the amino group to be condensed with the carboxyl group of the next amino acid, by an acid solution such as trifluoroacetic acid or methanesulfonic acid. The salt thus formed by deprotection is then neutralized such as with triethylamine or diisopropylethylamine. Condensation with the second amino acid is then effected in the presence of a dehydrating agent, preferably dicyclohexylcarbodiimide, usually at normal room temperature. The polymer is then washed, deprotected, neutralized and reacted with the next amino acid in the desired peptide sequence under the conditions set forth above. The desired peptide product is then obtained by treating the polymer with a strong acid such as hydrofluoric acid, hydrogen bromide/acetic acid or pdOAc/$H_2$ which effects cleavage of the peptide from the polymer while deprotecting any protected side chain groups. A particularly suitable deprotecting agent is hydrogen fluoride containing 10% anisole. The peptide is recovered by extraction into a weak acid such as acetic acid, 0.01H NCl or the like. This product then can be purified by chromatography.

The compositions of this invention are particularly useful for administration to animals, particularly humans for reducing blood pressure. Compositions of this invention can be administered intravenously. When administered alone, suitable dosages depend upon the inhibitor constant of the particular peptide being administered. The dosage should be sufficient to provide substantial inhibition of renin while at the same time not be so large as to substantially increase the risk of orthostatic hypotension. Generally suitable dosages are between about 0.2 and about 2 mg per kg body weight. The inhibition constant of a composition of this invention is determined by the degree with which the composition inhibits reaction of renin with its substrates. This is determined as follows:

The peptide being tested is dissolved in 0.01 N HCl and the pH adjusted to pH 7.5 to obtain high concentrations of peptide. The peptide solution is diluted further to appropriate concentrations with 0.1 M Tris HCl-albumin.

First, to determine $K_m$, renin (0.006 Goldblatt unit/ml) is incubated for 2 hrs. at 37° with incremental concentrations of tetradecapeptide substrate varying between 3 and 108μ M in a volume of 160 μl at pH 7.5 in 0.1M Tris HCl containing 0.5% albumin. The release of angiotensin I is determined by radioimmunoassay (Haber et al, J. Clin. Endocrinol. Metab. 29, 1349 (1969)). To determine the inhibitor constant ($K_i$) a parallel series of experiments are performed exactly as described above but in the presence of a single concentration (1–100μ M) of the inhibitory peptide which gives 50% inhibition. The cross-reaction of the tetradecapeptide with antibody is about 1% and less than 0.5% with the renin inhibitors both before and after exposure to renin. Controls for cross-relatively are performed with each experiment and appropriate corrections are made when significant, (Poulsen et al, Scand. J. Clin. Lab. Invest. 31, Suppl. No. 132, 1, (1973)).

The inhibitor constant is calculated at previously described, (Poulsen et al, Scand. J. Clin. Lab. Invest. 31, suppl. No. 132, 1, (1973)), from a weighted leastsquares fit of a Lineweaver-Burk plot. Each point is given a weight proportional to the initial velocity, (Dowd et al, J. Biol. Chem. 240, 863, (1965)).

To determine $K_m$ in plasma, 20 μl aliquots of serial dilutions of plasma are incubated with 5 μl of human renin ($4 \times 10^{-3}$ GU/ml); 5 μl of a solution containing 3M Tris HCl (pH 7.3), 200 mM EDTA, 12 mM 2,3-dimercaptopropanol, and 25 mM 8-hydroxyquinoline; and 10 µl of 0.1M Tris HCl (pH 7.5) containing 0.5% albumin. The mixture is incubated for 45 min at 37° and then cooled to 0°. Complementary amounts of plasma are then added as 20 µl of a plasma dilution in 0.1M Tris HCl (pH 7.5) containing 0.5% albumin to give the same amount of plasma protein in all tubes. Tracer and antibody (1000 µl) and then added following the radioimmunoassay procedure described by Poulsen et al, (J. Clin. Endocrinol. Metab. 39, 816, (1974)). Data for the standard curve is collected in the same medium kept at 4°. To determine $K_i$, parallel series of experiments are performed in which the 10 µl Tris buffer is replaced with 10 µl of a solution containing between 2–100µ M inhibitor, respectively.

Having now generally described this invention, the same will become better understood by reference to certain specific examples which are included herein for purposes of illustration only, and are not intended to be limiting of the invention unless otherwise specified.

EXAMPLE 1

Synthesis and Testing of D-RIP

This example illustrates the preparation of the decapeptide, Pro-His-Pro-Phe-His-Phe-Val-Try-D-Lys (D-RIP).

Peptide Synthesis tert-Butyloxycarbonylamino acids were purchased from Peninsula Inc. (San Mateo, CA). Side chain protecting groups were: histidine, tosyl; tyrosine, 2-bromobenzyloxycarbony; lysine, 2-chlorobenzyloxycarbonyl. Tritiated proline was obtained from New England Nuclear (Boston, MA), diluted to 0.5 Ci Mol$^{-1}$ with unlabeled proline (Eastman Chemical Co., Rochester, NY) and converted to the tertbutyloxycarbonyl derivative with di-t-butylpyrocarbonate (Tridom, Hauppage, NY). Triethylamine was purchased from Pierce Chemical Co. (Rockford, IL), trifluoroacetic acid was obtained from Halocarbon (Hackensack, NJ). Dichloromethane was distilled from CaH$_2$ before used. The support for synthesis was LS-601 Merrifield Resin containing 0.75 mMol Cl g$^{-1}$ (Laboratory Systems Inc., San Mateo, CA). Other reagents were of analytical grade.

Synthetic reactions were performed in 60 mL polypropylene syringes fitted with a polyethylene frit using apparatus and techniques previously described (Burton et al, Biochemistry, 14:3892, 1975).

Protocol for the synthesis was constructed by a computer program. Amino acid analyses were performed on a Durrum D-500 analyzer and the best fit observed and theoretical composition obtained with a computer program. High pressure liquid chromatography was done with a 410 system (Beckman Instruments, Inc. Palo Alto. CA) eluted through a 178.32 flow cell (Hellma, Jamaica, NY) in the HP 8450 spectophotometer (Hewlett Packard, Palo Alto, CA). A wavelength chromatography program was used to construct an elution profile at multiple wavelengths. A Beckman ODS 10×250 mM column was used for the analysis of the peptide. Other apparatus used in characterization has been described (Poulsen et al, Biochemistry 12 3877, 1973).

The solid phase synthesis of D-RIP (RI-71) was begun with 2.89 g amino acyl polymer containing 377 micromoles protected D-lysine. Synthesis was effected using standard techniques with a 5-fold excess of the appropriate amino acid, a 5-fold excess of Et$_3$N and a 5-fold excess of the coupling reagent LeBop. The N-terminal prolyl residue was incorporated as the tritiated derivative. On completion of synthesis 3.02 g of protected peptidyl-polymer was obtained (86%). Treatment of 3.02 g of this material with 30 mL HF-10% anisole for 1.25 hr at 0° followed by evaporation at high vacuum yielded the cleaved resin which was transferred to a coarse sintered glass funnel with 25 mL cold AcOEt. The resin was then extracted with 400 mL 5% AcOH and the AcOH extract lyophilized to yield a white powder (92%). 391 mg of this material was dissolved in 20 ml AcOH solution with heating and the solution centrifuged to remove a small precipitate. The supernatant was chromatographed on Sephadex G-25 (2.5×115 cm) in the same solvent at a flow rate of 91 mL hr$^{-1}$. Fractions containing the desired material eluted between 660 and 1170 ml and were pooled and lyophilized to yield the product (80%).

Lys, 1.04; Tyr, 0.91; Val. 0.85; Phe 2.89; His 2.03; Pro, 2.20. Percent peptide 58.4%, Minimum variance, 0.017. Mol. Wt. 1318.46. Molar extinction coefficient (280 nM) 1403; specific activity, 0.419 Ci Mol$^{-1}$, tlc: R$_F$ (T3) 0.71, R$_F$ (T4) 0.03. R$_F$ (T6) 0.70. K$_I$ 29.5 micromolar. Solubility 0.33 mM; log P= −1.28. hplc homogeneous (ODS column, linear gradient 20-45%CH$_3$CN-0.2%, TfaOH, 40 minutes, A$_{280}$

In Vitro Testing

Angiotensin I standards and tetradecapeptide renin substrate were obtained from Peninsula (San Mateo, CA). Angiotensin I concentrations were determined with the radio immunoassay kit purchased from New England Nuclear (Boston, MA). Procedure for determination of angiotensin I concentration was followed as outlined in instructions contained in the radioimmunoassay kit.

For K$_I$ determinations tetradecapeptide solutions having a concentration of 75, 60, 50, 40, 30, and 20 micromolar were prepared by dissolving tetradecapeptide in 0.01N HCl and diluting to the appropriate concentration with 0.1M Tris-01% lysozyme buffer (pH 7.4). 50 microliters of renin solution (V3) was diluted 100 fold, with Tris-lysozyme buffer, D-RIP was dissolved at a concentration of 100 and 50 micromolar in the same buffer. For the uninhibited reaction Tris-lysozyme buffer alone was used in place of the inhibitor solution.

Incubation mixtures containing TDP solution (150 microliters), renin solution (50 microliters), and the inhibitor (50 microliters) were incubated for 1 hr at 37°, cooled to 4° and assayed for angiotensin I concentration.

Data from the RIA was worked up using a computer program. Data were first fitted to a Lineweaver-Burke plot and from this K$_I$ was calculated.

In Vivo Testing

Animal Model

The animal mode of acute renovascular hypertension was prepared by surgically implanting an inflatable cuff about the aorta above the left kidney of an adult Macaca fascicularis. The right kidney was removed and catheters were implanted in the right iliac vein and artery. Two arterial catheters led from above and below the constricting cuff to a strain gage in order to measure blood pressure. Inflation of the cuff created a measurable amount of ischemia to the remaining kidney and renin dependent hypertension developed in about one hour.

Response of Infused Pharmacological Agents

Since the infusion of some agents requires the prolonged infusion of 5% dextrose in water (D5W), the effects of the infusion were examined. A solution of D5W was infused overnight at three mL $hr^{-1}$ in normal monkeys with the cuff inflated. Neither blood pressure nor heart rate changed as a result of the infusions.

The results of the infusion of D-RIP (RI-71) are summarized below. Infusion of the D-RIP over a period of four hours reduced the blood pressure increase induced by inflation of the suprarenal cuff by onehalf. As expected, plasma renin levels rose during constriction of the cuff.

| | Sodium State | Blood Pressure (Torr) | Heart Rate (bpm) | Plasma Renin Activity ng Ang I $mL^{-1}$ $hr^{-1}$ |
|---|---|---|---|---|
| Control | Replete | 112 | 165 | 6.8 |
| Cuff Inflated | | | | |
| 1.0 hr | " | 122 | 160 | 17.8 |
| + D-RIP | | | | |
| 1.0 hr | " | 118 | 155 | 19.2 |
| 2.0 hr | " | 116 | 145 | 18.2 |
| 3.0 hr | " | 115 | 140 | 17.9 |
| 4.0 hr | " | 116 | 135 | 21.8 |

EXAMPLE 2

TABLE

| Comparison between RIP and D-RIP | RIP | D-RIP |
|---|---|---|
| Solubility (pH 7.40) | 840 μM | 330 μM |
| $K_i$ | 42 μm | 29.5 μm |
| Degradation by proteolytic enzyme | + | – |
| Oral Activity | – | – |
| Half life in vivo | 3.8 min | 5 min |
| Substrate for Converting Enzyme | + | – |
| Crossreactivity with Antisera against Angiotensin I | + | – |

TABLE-continued

Finally, it has been noted that D-RIP does not inhibit converting enzyme while, to a small degree, RIP does.

Having now fully described this invention it will be understood by one of skill in the art that the same can be performed within a wide and equivalent range of structures, compositions, modes of administration conditions, and used without affecting the spirit or scope of the invention or of any embodiment thereof.

What is new and intended to be covered by Letters Patent of the United States is:

1. A compound of the formula

Z-His-Pro-Phe-His-X-X-Val-Tyr-(D-)-Y wherein the X's are the same or different and selected from the group consisting of aromatic, an aliphatic and a chlorinated aliphatic amino acid phenylalanine, tyrosine, mono-chloro phenylalanine, leucine, isoleucine, valine and glycine;

Y is selected from the group consisting of lysine, arginine, ornithine, aspartic acid, glutamic acid, and their alpha-carbon esters of lower aliphatic alcohols, and alpha-carbon primary or secondary lower aliphatic amides; and Z is a proline, hydroxyproline, thioproline or a polyproline residue having up to 5 prolyl residues.

2. The compound of claim 1 wherein both Xs are phenylalanyl, Z is proline and Y is lysine.

3. A process for reducing blood pressure in an animal afflicted with high blood pressure related to renin excess, which comprises administering to said animal a blood pressure decreasing amount of a compound of claim 1.

4. The process of claim 3 wherein said compound is such that the Xs are phenylalanyl, Z is prolyl and Y is lysyl.

5. The process of claim 3 wherein said animal is a human.

6. A composition useful for reducing blood pressure related to renin in animals which comprises a blood pressure decreasing amount of a compound of the formula of claim 1, together with a pharmaceutically inert carrier.

* * * * *